US006895079B2

(12) United States Patent
Birdwell et al.

(10) Patent No.: US 6,895,079 B2
(45) Date of Patent: May 17, 2005

(54) MULTIPLE FOCAL SPOT X-RAY INSPECTION SYSTEM

(75) Inventors: Thomas William Birdwell, Middletown, OH (US); John Robert Brehm, Middletown, OH (US); Andrew Joseph Galish, West Chester, OH (US)

(73) Assignee: General Electric Company, Schenectady, NY (US)

( * ) Notice: Subject to any disclaimer, the term of this patent is extended or adjusted under 35 U.S.C. 154(b) by 48 days.

(21) Appl. No.: 10/224,174

(22) Filed: Aug. 20, 2002

(65) Prior Publication Data

US 2004/0037393 A1 Feb. 26, 2004

(51) Int. Cl.[7] .................................................. H01J 35/30

(52) U.S. Cl. ........................................ 378/137; 378/147

(58) Field of Search ............................ 378/4, 9, 11, 12, 378/19, 113, 119, 124, 136, 137, 138, 143, 144, 145, 147

(56) References Cited

U.S. PATENT DOCUMENTS

| | | | | |
|---|---|---|---|---|
| 4,002,917 A | * | 1/1977 | Mayo | 378/14 |
| 4,250,425 A | * | 2/1981 | Gabbay et al. | 378/125 |
| 4,521,902 A | | 6/1985 | Peugeot | 378/138 |
| 4,637,040 A | | 1/1987 | Sohval et al. | 378/9 |
| 4,689,809 A | * | 8/1987 | Sohval | 378/136 |
| 5,119,408 A | | 6/1992 | Little et al. | 378/4 |
| 5,128,864 A | | 7/1992 | Waggener et al. | 364/413.21 |
| 5,335,255 A | * | 8/1994 | Seppi et al. | 378/4 |
| 5,467,377 A | | 11/1995 | Dawson | |
| 5,550,889 A | | 8/1996 | Gard et al. | 378/113 |
| 5,706,326 A | | 1/1998 | Gard | 378/19 |
| 5,712,889 A | | 1/1998 | Lanzara et al. | |
| 6,041,132 A | | 3/2000 | Isaacs et al. | 382/100 |
| 6,118,839 A | | 9/2000 | Dafni et al. | 378/15 |
| 6,122,344 A | | 9/2000 | Beevor | 378/88 |
| 6,125,167 A | * | 9/2000 | Morgan | 378/124 |
| 6,229,870 B1 | * | 5/2001 | Morgan | 378/9 |
| 2002/0097836 A1 | | 7/2002 | Grodzins | |

FOREIGN PATENT DOCUMENTS

| | | |
|---|---|---|
| DE | 3021 757 A1 | 12/1981 |
| EP | 1 005 257 A2 | 5/2000 |

* cited by examiner

*Primary Examiner*—Edward J. Glick
*Assistant Examiner*—Courtney Thomas
(74) *Attorney, Agent, or Firm*—Adams Evans P.A.; V. G. Ramaswamy

(57) ABSTRACT

An X-ray inspection system includes an X-ray source that generates more than one beam defining an inspection plane, the beams being substantially parallel to each other; an X-ray detector having a plurality of detector arrays, each of which is aligned with one of the beams, and structure for supporting an object between the X-ray source and the X-ray detector. The X-ray source includes an electron gun and a device for steering an electron beam generated by the gun to multiple focal spots on a target.

7 Claims, 4 Drawing Sheets

MULTIPLE FOCAL SPOT X-RAY INSPECTION SYSTEM

CROSS REFERENCE TO RELATED APPLICATIONS

BACKGROUND OF THE INVENTION

This invention relates generally to X-ray inspection systems and more particularly to X-ray inspection systems using a multiple focal spot source.

It is known to inspect industrial parts with X-rays, for example using digital radiography (DR) or computed tomography (CT). The X-ray sources used for these methods produce X-rays by accelerating electrons into a dense (generally tungsten) target. The number of X-rays produced is limited primarily by the ability to cool the areas on the target where the electrons strike. Inspection time is directly related to the X-ray output, which is directly related to the focal spot size. However, focal spot size is inversely related to image resolution. Therefore, trade-offs must be made between inspection speed and image quality. Also, X-ray detection devices include linear X-ray detectors, which offer excellent scatter rejection and are well suited for computed tomography. However, because the X-ray beam is collimated into a linear slice, it does not maximize use of the available conical X-ray source yield. This results in increased inspection time and cost.

Accordingly, there is a need for a method and apparatus to improve X-ray source utilization.

BRIEF SUMMARY OF THE INVENTION

The above-mentioned need is met by the present invention, which provides an X-ray inspection system which comprises an X-ray source having means for generating more than one beam which defines an inspection plane, the beams being substantially parallel to each other; an X-ray detector having more than one detector array, each of which is aligned with one of the inspection planes; and means for supporting an object between the X-ray source and the X-ray detector. The means for generating more than one beam may include an electron gun and means for steering an electron beam generated by the gun to multiple focal spots on a target.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
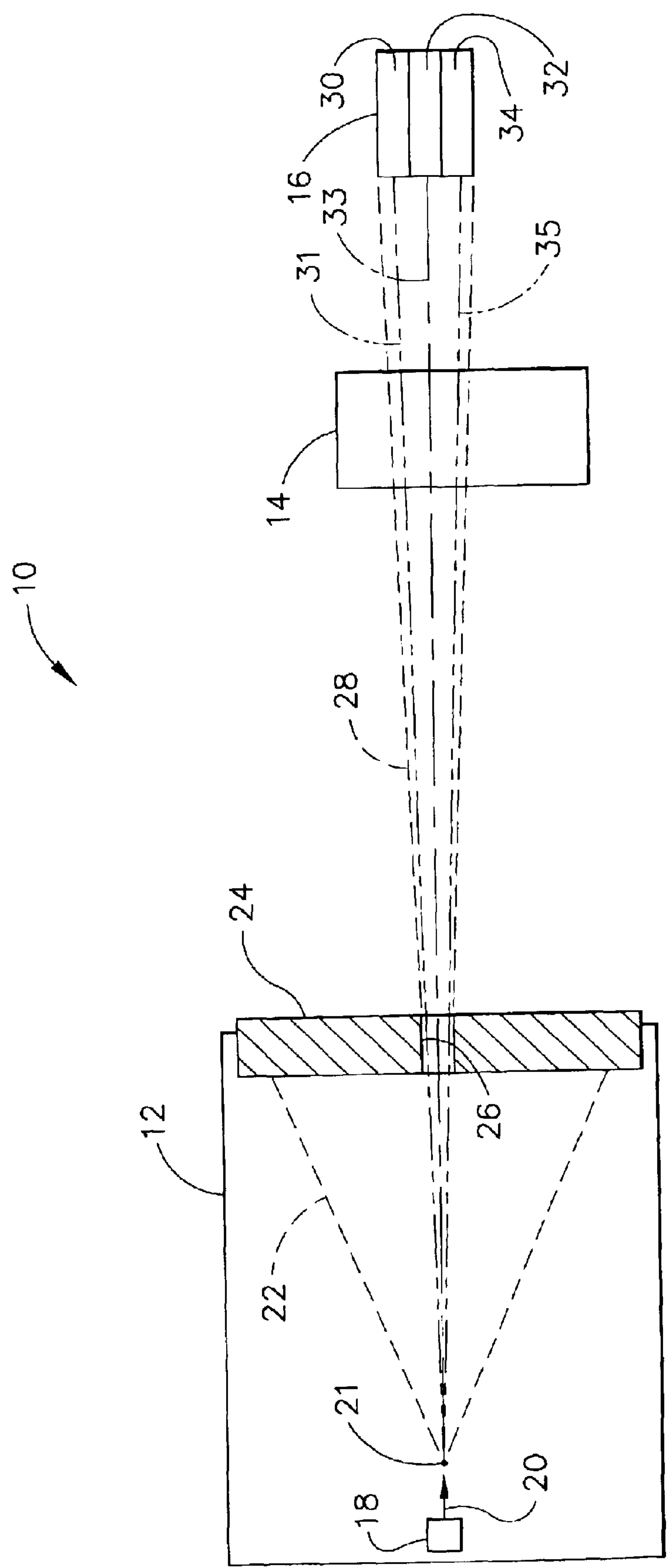
FIG. 1 illustrates a schematic side view of a prior art X-ray inspection system.

Referring to the drawings wherein identical reference numerals denote the same elements throughout the various views, FIG. 1 shows a schematic side view of a prior art X-ray inspection system 10. The system 10 includes an X-ray source 12 and a detector assembly 16 disposed on opposite sides of an object 14 (for example, a gas turbine engine component to be inspected). The source 12 comprises an electron gun 18 which directs a beam of electrons 20 onto a focal spot 21 of a target (not shown) of a dense material such as tungsten. This causes a beam of X-rays 22 to emanate from the target. The X-ray beam 22 strikes a source collimator 24 having an aperture 26. A portion of the X-ray beam 22 exits the aperture 26 as X-ray output beam 28. The output beam 28 passes through the object 14, where it is attenuated to varying degrees depending upon the density and structure of the object 14. The output beam 28 then strikes a detector assembly 16, which in this example comprises three adjacent linear detector arrays 30, 32, and 34.

The X-ray inspection planes (labeled 31, 33, and 35 in FIG. 1) of this prior art apparatus are not parallel because they must all contain the focal spot 21. There are a number of known computational methods that may be used to alleviate this problem, however these methods have limitations in terms of accuracy, time and cost because of the complexity of the required computations. Additionally, because the aperture 26 of X-ray source collimator 24 must be of a sufficiently large dimension to allow illumination of all of the detector arrays by a single X-ray beam, scatter rejection, and hence image quality is reduced.

Figure 2:
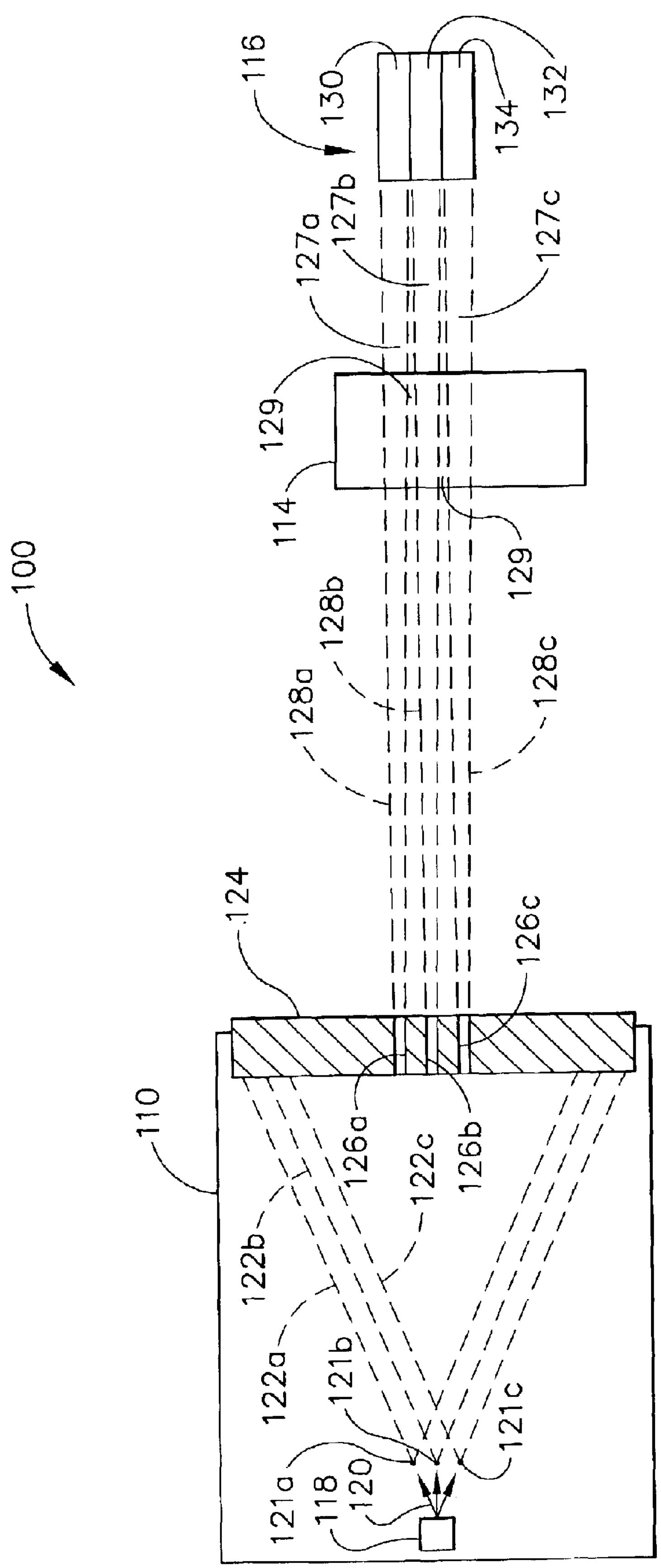
FIG. 2 illustrates a schematic side view of an X-ray inspection system constructed in accordance with the present invention.
Figure 3:
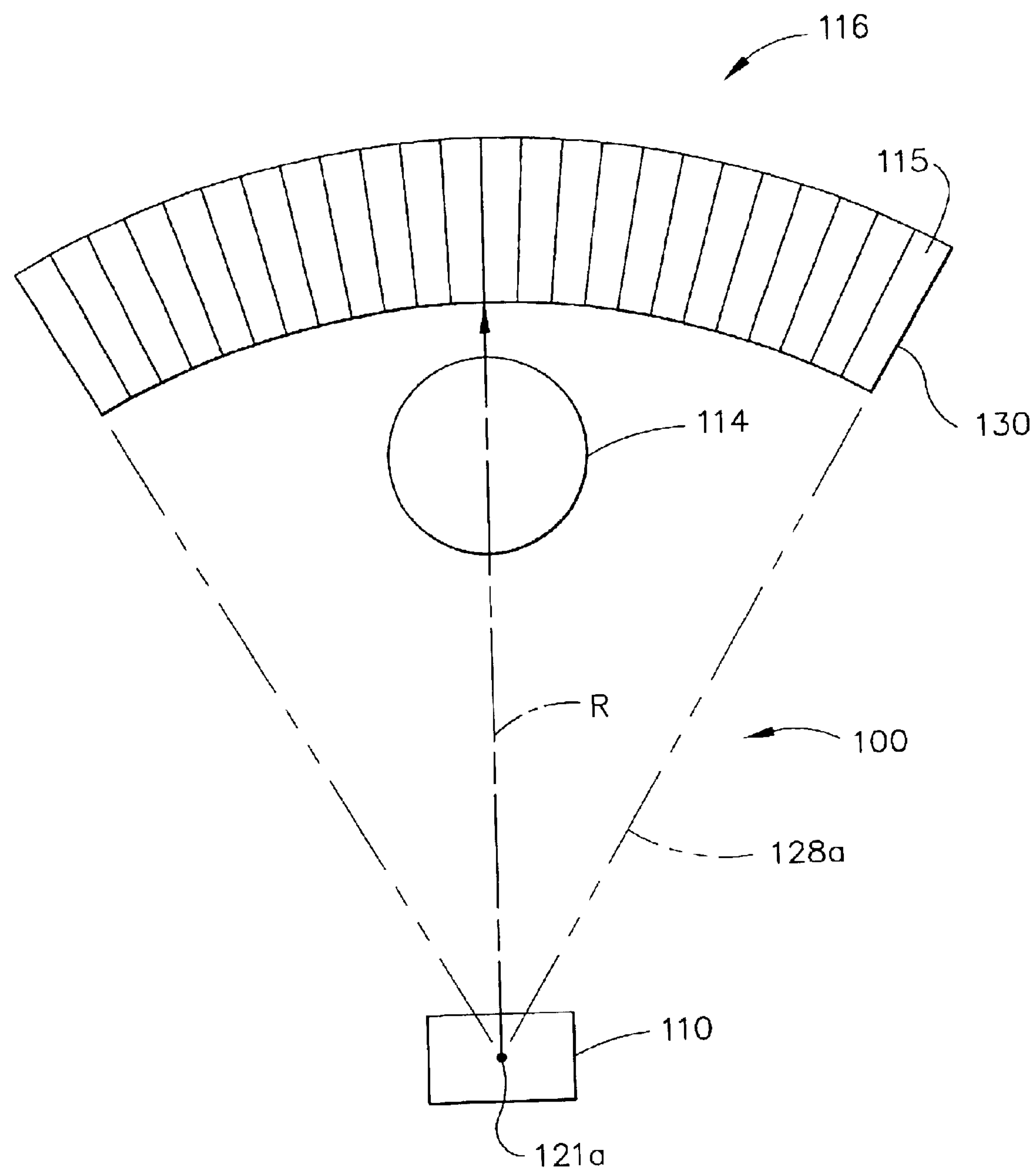
FIG. 3 is a schematic top view of the X-ray inspection system of FIG. 2.

An exemplary X-ray inspection system 100 constructed in accordance with the present invention is illustrated in FIG. 2. Although the illustrated system has three focal spots, the present invention is not limited to that number and a greater or lesser number of focal spots may be used. The system 100 includes an X-ray source 110 and a detector assembly 116 disposed on opposite sides of an object 114 (for example, a gas turbine engine component to be inspected). The X-ray source 110, detector assembly 116, and object 114 are supported in the relative positions depicted in FIG. 2 by known means, which are not shown. For example, the source 110 and detector assembly 116 may be suspended by a gantry, while the object 114 may be supported between them on a pedestal, a turntable, or a part manipulator. The source 110 includes an electron gun 118 which emits a beam 120 of electrons. In the illustrated example, the electron beam 120 is sequentially deflected or "steered", as described in more detail below, onto focal spots 121*a*, 121*b*, 121*c* on a target (not shown) of a dense material, such as tungsten. This causes X-ray beams 122*a*, 122*b*, and 122*c* to emanate from the target. The X-ray beams 122 strike a source collimator 124 having apertures 126*a*, 126*b*, and 126*c*. A portion of the X-ray beams 122 exit the apertures 126 as fan-shaped X-ray output beams 128*a*, 128*b* and 128*c*. The output beams 128 pass through the object 114, where they are attenuated to varying degrees depending upon the density and structure of the target 114. The output beams 128 then strike the detector assembly 116, which in this example is shown as comprising three adjacent linear detector arrays labeled 130, 132, and 134 respectively. In the illustrated example, each of these arrays is an arc-shaped assembly of detector elements 115 which are radially aligned to the output beams 128, as shown in FIG. 3. Other detector shapes, such as a straight line array, could also be used.

The focal spots 121 are located within the X-ray inspection planes denoted 127*a*, 127*b* and 127*c* in FIG. 2, which are defined by the boundaries of the collimated X-ray output beams 128*a*, 128*b*, and 128*c*, respectively. As shown in FIG. 2, the output beams 128 are substantially parallel to each other. Furthermore, each focal spot 121 and its associated collimator aperture 126 and detector array are all aligned with their respective inspection plane 127. That is, the vertical spacing and position of the focal spots are selected so that each inspection plane 127 passes through a focal spot 121, a collimator aperture 126, and the center of a corresponding detector array. The thickness of the collimator 124 and the position and dimensions of the individual apertures 126 are selected to properly define the inspection planes 127 and to eliminate extraneous X-ray contribution. That is, each of the individual apertures 126 rejects X-ray contribution from any focal spots other than the one it is aligned with. As many focal spots, output beams, and detector arrays may be used as are necessary for a particular application.

The use of multiple focal spots to generate parallel spaced-apart X-ray beams as described above allows a relatively large area of an object 114 to be scanned in a given time period while minimizing X-ray scatter and efficiently utilizing the available X-ray output. As seen in FIG. 2, the use of multiple parallel beams results in void areas 129 of the object 114 which are not illuminated by X-rays and therefore do not contribute to scattering. Furthermore, the use of multiple focal spots 121 increases the effective area on the target compared to a single focal spot. Accordingly, each of the multiple focal spots 121 can have the same size and output characteristics as a single focal spot, while still remaining compatible with the mechanical and thermal properties of the target and its cooling capabilities. Each discrete focal spot 121 is located sufficiently distant from the others to allow increased total combined area for cooling, while maintaining each at a desired focal spot size.

Various means are known for scanning the electron beam 120 as depicted schematically in FIG. 2. For example, deflection coils may be used to create a variable electrical or magnetic field which is used to alter the direction of travel of the electron beam 120. Any known means which allows the creation of multiple focal spots 121 on the target may be used.

Figure 4:
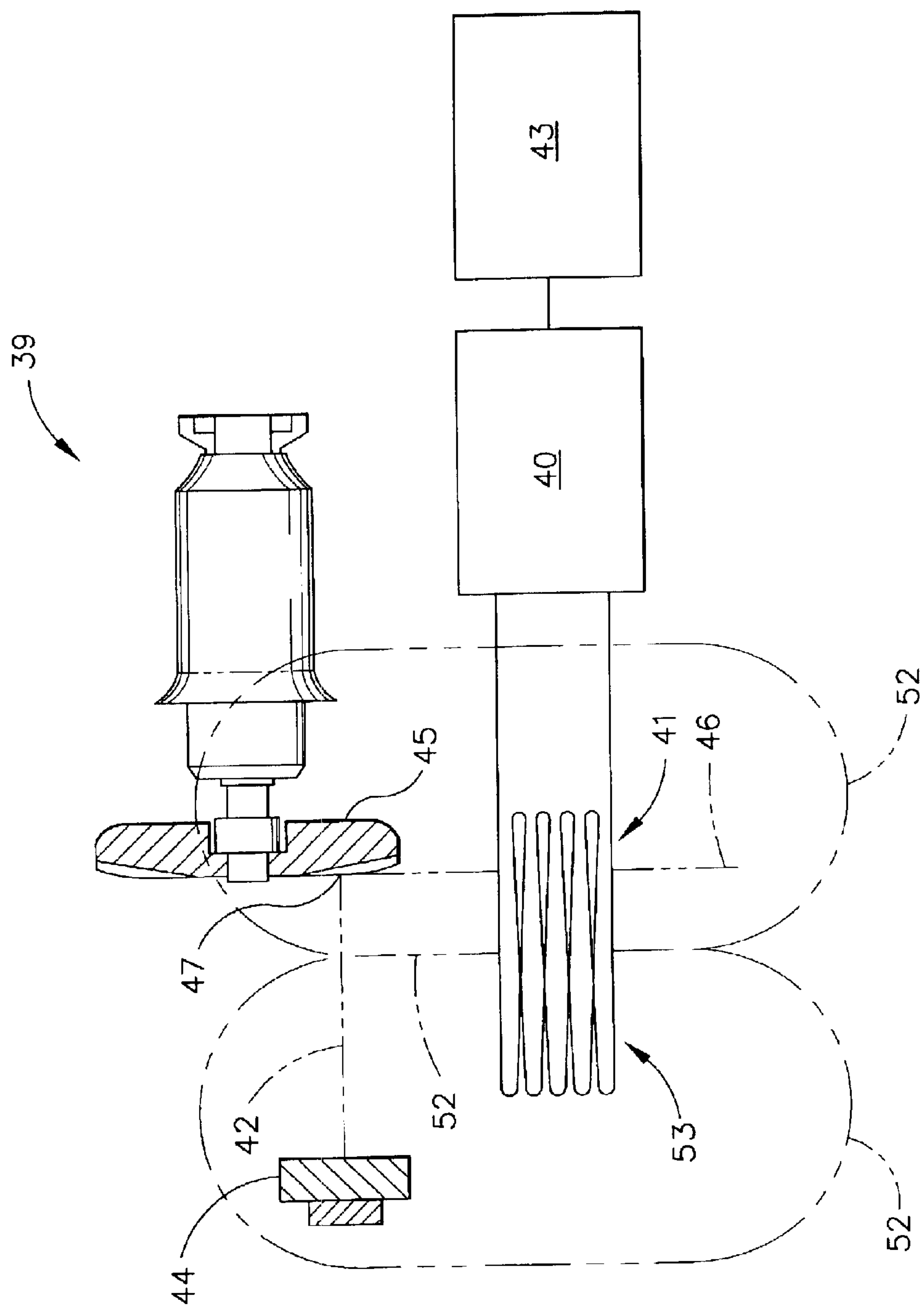
FIG. 4 shows an example of a beam steering mechanism.

One possible apparatus which could be used to create multiple X-ray beams is illustrated in FIG. 4. A variable current power supply 40 is connected to a deflection coil 41. The deflection coil 41 is mounted in an X-ray source 39 at a location near the path of an electron beam 42 produced in the X-ray source 39 by an electron gun 44. This electron beam 42 strikes the surface of a target 45 (for example a tungsten anode), and a beam of X-rays 46 is produced. The location on the surface of the target 45 where the electron beam 42 strikes is the focal spot 47.

The coil 41 produces a magnetic flux describing closed paths in a known manner, as indicated by dashed line 52. The geometrical relationship between the coil 41 and the electron beam 42 is chosen so as to develop a substantially uniform magnetic field substantially normal to the path of the electron beam 42. A force equal to the cross product of the velocity of the electron beam and the magnetic flux vector acts on the electron beam 42 to deflect the electron beam 42 and move the focal spot 47. In FIG. 4, the direction of the movement is perpendicular to the plane of the paper and the deflection coil 41 is positioned such that the generated X-rays pass through a central opening 53 therein. The direction of this movement is determined by the direction of current flow through the deflection coil 41, and hence the polarity of the input signal to the current supply 40. The input signal to the current supply 40 is provided by a controller 43 which may be any known device capable of providing a control signal, for example a computerized controller. In operation, the current flow to the coil 41 is varied so as to sequentially strike separate focal spots on the target 45. In this manner the beam is time-multiplexed proportionally to the number of focal spots. For example, if three focal spots are used, the electron beam would be directed to each of the focal spots for an average of one-third of the time the electron gun is operating. This beam deflection method may be used to create as many separate focal spots as desired.

The multiple focal spots of the present invention could also be created by using a multiple electron gun system (not shown), in which two or more individual electron guns are disposed adjacent to each other within the X-ray source, and each electron gun generates an electron beam which strikes a different focal spot on a target.

The foregoing has described an X-ray inspection system comprising an X-ray source having means for generating more than one beam defining an inspection plane, said beams being substantially parallel to each other; an X-ray detector having more than one detector array, each of which is aligned with one of said beams; and means for supporting an object between the X-ray source and said X-ray detector. The means for generating more than one beam may include an electron gun and means for steering an electron beam generated by the gun to multiple focal spots on a target. While specific embodiments of the present invention have been described, it will be apparent to those skilled in the art that various modifications thereto can be made without departing from the spirit and scope of the invention as defined in the appended claims.

What is claimed is:

1. An X-ray inspection system, comprising:

an X-ray source having more than one focal spot and means for generating more than one fan-shaped beam, each of said beams having an angular width measured in a first direction substantially greater than a thickness of said beam measured in a second direction perpendicular to said first direction, said beams being substantially parallel to each other and spaced apart in said second direction, wherein each beam defines an inspection plane and each of said focal spots is contained in one of said inspection planes, and wherein said means for generating more than one beam includes an electron gun operable to generate a beam of electrons and means for sequentially directing said beam of electrons to spaced-apart locations on a target to produce said focal spots;

an X-ray detector comprising a plurality of parallel arcuate detector arrays, each of said arrays being aligned with one of said inspection planes; and means for supporting an object between said X-ray source and said X-ray detector.

2. The X-ray inspection system of claim 1 wherein said X-ray source further includes:

a collimator having a number of apertures equal to the number of said focal spots, wherein each of said apertures is aligned with one of said inspection planes.

3. The X-ray inspection system of claim 1 wherein said beam is directed by using at least one electromagnetic field.

4. The X-ray inspection system of claim 3 wherein said at least one electromagnetic field is generated by at least one deflection coil.

5. A method for inspecting an object, comprising:

generating more than one X-ray beam from an X-ray source having more than one focal spot and an electron gun operable to generate a beam of electrons, said X-ray beams each defining an inspection plane, each of said beams having an angular width measured in a first direction substantially greater than a thickness of said beam measured in a second direction perpendicular to said first direction, said inspection planes being substantially parallel to each other and spaced apart in said second direction, wherein and said focal spots are produced by sequentially directing said beam of electrons to spaced-apart locations on a target;

providing an X-ray detector comprising more than one detector array, each of said arrays being aligned with one of said inspection planes; and providing means for supporting an object between said X-ray source and said X-ray detector.

6. The method of inspecting an object of claim 5 wherein said X-ray Source further includes:

a collimator having a number of apertures equal to the number of said focal spots, wherein each of said apertures is aligned with one of said inspection planes.

7. The X-ray inspection method of claim 5 wherein said beam of electrons is directed by using at least one electromagnetic field.

* * * * *